US011191731B2

(12) United States Patent
Schad et al.

(10) Patent No.: US 11,191,731 B2
(45) Date of Patent: *Dec. 7, 2021

(54) FILM COATING COMPOSITION AND METHODS OF MAKING AND USING THE SAME

(71) Applicant: Sensient Colors LLC, St. Louis, MO (US)

(72) Inventors: Beverly A. Schad, Union, MO (US); Brian K. Cheng, Chesterfield, MO (US)

(73) Assignee: Sensient Colors LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/191,772

(22) Filed: Nov. 15, 2018

(65) Prior Publication Data

US 2019/0321300 A1 Oct. 24, 2019

Related U.S. Application Data

(63) Continuation of application No. 15/352,258, filed on Nov. 15, 2016, now Pat. No. 10,159,650, which is a
(Continued)

(51) Int. Cl.
*A61K 9/28* (2006.01)
*A23P 20/10* (2016.01)
*A23G 3/34* (2006.01)

(52) U.S. Cl.
CPC ............ *A61K 9/2866* (2013.01); *A23G 3/343* (2013.01); *A23P 20/105* (2016.08); *A61K 9/282* (2013.01);
(Continued)

(58) Field of Classification Search
None
See application file for complete search history.

(56) References Cited

U.S. PATENT DOCUMENTS 3,802,896 A 4/1974 Westall et al.
3,882,228 A * 5/1975 Boncey ............... A61K 9/0007
424/489

(Continued)

FOREIGN PATENT DOCUMENTS

EP 0290194 11/1988
EP 1978063 10/2008
(Continued)

OTHER PUBLICATIONS

DuPont, "Opacity and whiteness" <http://www.specialchem4polymers.com/tc/titanium-dioxide/index.aspx?id-=benefits.sub.—opacity> SpecialChem, available as early as Apr. 7, 2010 (1 page).
(Continued)

*Primary Examiner* — Aradhana Sasan
(74) *Attorney, Agent, or Firm* — Michael Best & Friedrich LLP

(57) ABSTRACT

A film coating composition comprising a cellulosic polymer, an opacifying agent, and a fatty acid is disclosed herein. Also disclosed is a film coating composition comprising a cellulosic polymer, an opacifying agent, a plasticizing agent, and a polyol. The disclosed film coating compositions may be mixed with a solvent to produce a film coating suspension. The film coating suspension can be applied to a substrate, such as a nutritional supplement, pharmaceutical, tablet, capsule, softgel, granule, particle, food confectionary form, agricultural seed, and the like to form a film coating on the substrate. Methods of coating a substrate with the film coating suspensions are also provided.

14 Claims, 1 Drawing Sheet

Precipitated Calcium Carbonate

Ground Calcium Carbonate

Related U.S. Application Data continuation of application No. 13/105,725, filed on May 11, 2011, now Pat. No. 9,492,395.

(60) Provisional application No. 61/333,634, filed on May 11, 2010.

(52) U.S. Cl.
CPC .......... *A61K 9/2813* (2013.01); *A61K 9/2826* (2013.01); *A23V 2002/00* (2013.01); *A23V 2200/22* (2013.01); *A23V 2250/1578* (2013.01); *A23V 2250/188* (2013.01); *A23V 2250/51082* (2013.01); *A23V 2250/51084* (2013.01)

(56) References Cited

U.S. PATENT DOCUMENTS

| | | | |
|---|---|---|---|
| 4,828,845 A * | 5/1989 | Zamudio-Tena | A23G 3/42 426/5 |
| 4,931,286 A * | 6/1990 | Johnson | A61K 9/2866 424/480 |
| 5,000,945 A | 5/1991 | Kobayashi et al. | |
| 5,389,380 A | 2/1995 | Noda et al. | |
| 5,536,511 A | 7/1996 | Yatka | |
| 5,593,694 A | 1/1997 | Hayashida et al. | |
| 6,638,534 B1 | 10/2003 | Ishibashi et al. | |
| 6,699,318 B1 | 3/2004 | Virtanen | |
| 9,492,395 B2 | 11/2016 | Schad et al. | |
| 10,159,650 B2 * | 12/2018 | Schad | A61K 9/282 |
| 2004/0109853 A1 | 6/2004 | McDaniel | |
| 2004/0175407 A1 | 9/2004 | McDaniel | |
| 2005/0271724 A1 | 12/2005 | Clark et al. | |
| 2006/0233732 A1 | 10/2006 | Lezer | |
| 2007/0269650 A1 | 11/2007 | Leuninger et al. | |
| 2008/0245273 A1 | 10/2008 | Vyorkka et al. | |
| 2009/0054533 A1 | 2/2009 | Pareek et al. | |
| 2009/0069495 A1 | 3/2009 | Fichtner et al. | |
| 2009/0099203 A1 * | 4/2009 | Blyth | A61K 9/2018 514/255.05 |
| 2009/0238811 A1 | 9/2009 | McDaniel et al. | |
| 2010/0041809 A1 | 2/2010 | Cavalier et al. | |
| 2010/0203190 A1 * | 8/2010 | Barkalow | A23G 1/54 426/5 |
| 2011/0048281 A1 * | 3/2011 | Durig | A61K 9/2866 106/203.1 |
| 2011/0129584 A1 | 6/2011 | Myers et al. | |
| 2013/0095141 A1 | 4/2013 | Schad et al. | |

FOREIGN PATENT DOCUMENTS

| | | |
|---|---|---|
| JP | 08034727 | 2/1996 |
| WO | 9830341 | 7/1998 |
| WO | 9903449 | 1/1999 |
| WO | 0048574 | 8/2000 |
| WO | 0203967 | 1/2002 |
| WO | 2008122617 | 10/2008 |

OTHER PUBLICATIONS

Specialty Minerals, "What is PCC—Precipitated Calcium Carbonate?" <http://www.specialtyminerals.com/our-minerals/what-is-pcc/> Our Minerals, available as early as Apr. 7, 2010 (3 pages).

Tier et al. "Production of precipitated calcium carbonate from calcium silicates and carbon dioxide" Energy Conversion and Management, Jan. 1, 2005, 46, 2954-2979.

Wikipedia, "Acid dissociation constant" <http://en.wikipedia.org/wiki/Acid.sub.—dissociation.sub.--constant&g-t; webpage last updated Dec. 13, 2011 (23 pages).

Wikipedia, "Coconut oil" <http://en.wikipedia.org/wiki/Coconut.sub.--oil> webpage last modified Jan. 4, 2012 (8 pages).

PCT/US2011/036121 International Search Report and Written Opinion dated Jan. 2, 2012 (10 pages).

European Patent Office Action for Application No. 11720951.0 dated Jun. 12, 2015 (4 pages).

* cited by examiner

Precipitated Calcium Carbonate
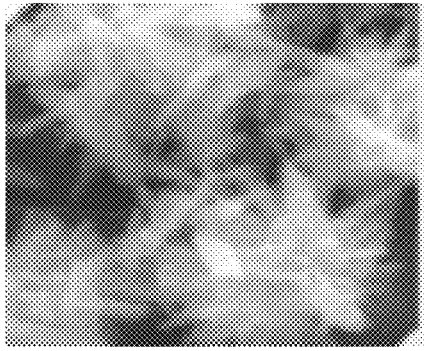
Ground Calcium Carbonate
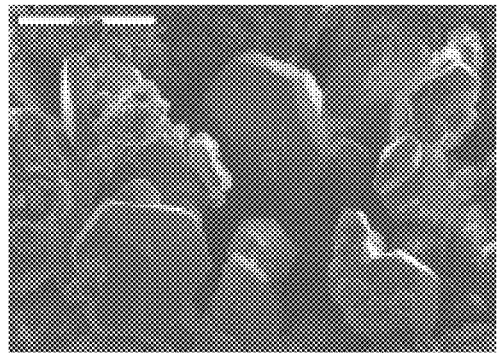

FILM COATING COMPOSITION AND METHODS OF MAKING AND USING THE SAME

CROSS REFERENCE TO RELATED APPLICATIONS

This application claims priority under 35 U.S.C. § 119(e) to U.S. Provisional Patent Application No. 61/333,634, filed on May 11, 2010 and hereby incorporated by reference in its entirety.

BACKGROUND

Film coating is an effective way of providing physical and chemical protection for a substrate. Film coatings include film forming agents—generally polymers that are soluble or dispersible in a solvent. Various additives may be used to facilitate the coating process and/or obtain specific coating properties. Ideally, film coatings should be stable, economical, and easy to process and should use food-approved ingredients to facilitate commercial implementation.

SUMMARY

Aspects of the disclosure provide film coatings, film coating compositions, film coating suspensions, as well as methods for making the same.

In an aspect, the disclosure provides a film coating composition. In some embodiments, the film coating composition may comprise film forming agent, an opacifying agent, and a fatty acid. In other embodiments, the film coating composition may comprise a film forming agent, an opacifying agent, a plasticizing agent, and at least one of a polyol and inulin, wherein the polyol, if present, is present in the composition in an amount from about 3% to about 25% of the composition by weight.

In another aspect, the disclosure provides a film coating suspension. In some embodiments, the film coating suspension may comprise a film forming agent, an opacifying agent, a fatty acid, and a solvent. In other embodiments, the film coating suspension may comprise a film forming agent, an opacifying agent, a plasticizing agent, a polyol, and a solvent.

In another aspect, the disclosure provides a substrate coated with a film coating. In some embodiments, the film coating may comprise a film forming agent, an opacifying agent, and a fatty acid. In other embodiments, the film coating may comprise a cellulosic polymer, an opacifying agent, a plasticizing agent, and a polyol, wherein the polyol is present in an amount from about 3% to about 25% of the film coating by weight.

In an aspect, the disclosure provides a method of coating a substrate. In some embodiments, the method may comprise applying a film coating suspension to a substrate to form a film coating thereon. In some embodiments, the film coating suspension may comprise a film forming agent, an opacifying agent, a fatty acid, and a solvent. In some embodiments, the film coating suspension may comprise a film forming agent, an opacifying agent, a plasticizing agent, a polyol, and a solvent.

Other aspects and embodiments of the disclosure will become apparent to one of skill in the art in light of the following description.

BRIEF DESCRIPTION OF THE DRAWINGS

FIG. 1 depicts exemplary crystal morphologies of precipitated calcium carbonate and ground calcium carbonate.

DETAILED DESCRIPTION

The disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures, components, or method steps are not meant to be construed to indicate any specific structures, components, or steps, or any particular order or configuration to such structures, components, or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Similarly, if a concentration is stated as at least 12%, it is intended that all values including and above 12%, such as 12%, 15%, 50%, 89%, etc., are expressly enumerated in the specification. In a further example, if a concentration is stated as less than 70%, it is intended that all values less than or equal to 70%, such as 1%, 8%, 45%, and 70%, are expressly enumerated in the specification. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of any such reference states only what the author(s) of the reference assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The disclosure generally relates to affordable, easy-to-use film coating compositions. When mixed with one or more solvents, the disclosed film coating composition may form a film coating suspension. The disclosed film coating suspensions may have high solution solids content, low viscosity, and/or low foam. When applied to a substrate, the film coating suspensions may form a film coating. The disclosed film coatings may possess one or more of the following characteristics: stability at high temperature and/or humidity, high slip, high brightness, high whiteness, low heavy metals content, high opacity, high adhesion, and/or high color stability. Suitably, the disclosed film coating compositions, film coating suspensions, and film coatings may be stable, economical, and easy to use, offering simple, rapid, and efficient processing. In embodiments, the disclosed film coating compositions, film coating suspensions, and film coatings can be used for coating substrates such as, for example, nutritional supplements, pharmaceuticals, tablets, capsules, softgels, granules, particles (e.g., micro- and nanoparticles), food confectionary forms, agricultural seeds, and the like.

The disclosure provides film coating compositions, film coating suspensions, and film coatings comprising at least one of a film forming agent, an opacifying agent, a complexing agent, a plasticizing agent, a lubricant, an antioxidant, a colorant, and combinations thereof. At least one of these materials can be approved for food use.

A film forming agent may provide smooth film-forming coating suspensions and enhance the rheological mechanical strength properties of film coating gel matrices. Film forming agents include, for example, polyvinylpyrrolidone, natural gums, starches, and cellulosic polymers. A cellulosic polymer may include a molecule comprising at least one cellulose polymer or derivative modified with small amounts of propylene glycol ether groups attached to the cellulose anhydroglucose chain affording binding properties that enhance the reinforcing film properties of film applications. Examples of cellulosic polymers include, but are not limited to, hydroxypropyl methyl cellulose ("HPMC"), carboxymethyl cellulose ("CMC") or salts thereof, hydroxypropyl cellulose ("HPC"), methylcellulose ("MC"), hydroxyethyl cellulose ("HEC"), and the like. In addition, cellulosic polymers may be characterized as ionic or non-ionic. Ionic cellulosic polymers include, for example, sodium CMC. Non-ionic cellulosic polymers include, for example, HPMC, HPC, HEC, and MC. A variety of commercially available cellulosic polymers exist and may include, for example, Spectracel™ HPMC compositions (available from Sensient Technologies).

Opacifying agents include, for example, clays and divalent salts such as zinc oxides, dicalcium phosphate, dicalcium phosphate dehydrate, tricalcium phosphate, calcium carbonate, and precipitated calcium carbonate. The disclosed opacifying agents provide film coatings with excellent brightness, whiteness, and/or opacity without using compounds containing heavy metals. For example, precipitated calcium carbonate exhibits a surface morphology characterized by long, hard needles (FIG. 1) that afford increased surface area capable of angular reflectance, providing high opacity, brightness, and whiteness. In some embodiments, the opacifying agent can stabilize one or more natural colorants in the disclosed compositions, suspensions, and/or coatings as disclosed in U.S. patent application Ser. No. 12/927,844, entitled Natural Blue-Shade Colorants and Methods of Making and Using Same, filed on Nov. 24, 2010, which is hereby incorporated by reference. Precipitated calcium carbonate can be prepared by any suitable method known in the art. In aqueous solution, opacifying agents comprising divalent salts yield various ionic dissociation products (collectively referred to herein as "dissociation species"). For example, calcium carbonate and precipitated calcium carbonate yield various dissociation species in aqueous solution such as, for example, $H^+$, $OH^-$, $CA_2^+$, $CO_3^{2-}$, $HCO_3^-$, and $CaHCO_3^+$.

A complexing agent may capture dissociation species and/or minimize or prevent dissociation of an opacifying agent. Complexing agents include, for example, inulin, polyols (e.g., xylitol), and fatty acids (e.g., oleic acid). Inulin is an oligosaccharide comprising fructose units linked by β (2-1) bonds. Inulin may be obtained using any suitable method and/or source. For example, some embodiments provide for inulin that can be derived from natural sources such as chicory, garlic, asparagus, onion, leek, banana, and Jerusalem artichoke. Commercially available sources of inulin include, for example, Orafti® P95 and Orafti® HSI (available from BENEO, Inc.). Polyols, also known as sugar alcohols, are organic compounds having multiple hydroxyl groups. Polyols include, but are not limited to, xylitol, maltitol, sorbitol, mannitol, erythritol, and lactitol. Fatty acids are organic compounds including a hydrocarbon chain and a terminal carboxylic acid group, and the hydrocarbon chain can be of any length from about 2 to about 30 carbons and can be saturated, monounsaturated, or polyunsaturated. Examples of fatty acids include, but are not limited to, oleic acid, stearic acid, palmitic acid, and triglyceride esters of oleic acid.

A plasticizing agent may enhance film characteristics of the disclosed film coatings, such as adhesion, flexibility, permeability, and the like. In some embodiments, the disclosed plasticizing agents can plate or coat the opacifying agent (e.g., precipitated calcium carbonate), providing a barrier to protect the opacifying agent from the surrounding liquid or atmospheric environment. In some embodiments, the disclosed plasticizing agents can promote film coating brightness and whiteness. In embodiments, plasticizing agents can include, but are not limited to, propylene glycol dicaprylate/dicaprate, medium chain triglycerides (such as, for example, C6 to C12 fatty acid esters of glycerol, fractionated coconut oil, and the like), glyceryl monostearate, propylene glycol, polypropylene glycol, polyethylene glycol, triacetin, glycerin, dibutyl sebacate, triglycerides, acetylated monoglycerides, glycerol monstearates, glycerin monostearate, oleic acid, stearic acid, sorbitol, tributyl citrate, acetyltributyl citrate, dibutyl phthalate, triethyl citrate, triethanolamine, aqueous emulsions of glyceryl monostearate and triethyl citrate, and combinations thereof. Commercially available plasticizing agents include, for example, Miglyol® 840 and Neobee® M-20 propylene glycol dicaprylate/dicaprate (available from Sasol GmbH and Stepan Co., respectively) and Neobee® M-5 medium chain triglycerides from fractionated coconut oil (available from Stepan Co.).

A lubricant may enhance esophageal transit ease, film slipperiness, and surface flowability. Examples of lubricants include, but are not limited to, talc, metallic stearates, silicon dioxide, sodium stearyl fumarate, palmitic acid, fatty acid esters, fatty acids, fatty alcohols, mineral oil, paraffins, leucine, polyethylene glycols, metallic lauryl sulfates, stearic acid, hydrogenated vegetable oil, triethyl citrate, PEG 3350, and combinations thereof.

An antioxidant may improve stability of the film coating compositions, film coating suspensions, and film coatings by reducing or preventing oxidation. Antioxidants include, but are not limited to, sodium ascorbate, tocopherols, carotenes, and the like.

Examples of colorants include dyes, lakes, and pigments and may include, but are not limited to, titanium dioxide, iron oxides, dyes such as, for example, FD&C Lakes, Carmine Lake, FD&C Blue no. 1, FD&C Blue no. 2, FD&C Red no. 3, FD&C Red no. 40, FD&C Yellow no. 5, FD&C Yellow no. 6, FD&C Green no. 3, alumina, talc, annatto extract, calcium carbonate, canthaxanthin, caramel, β-carotene, carmine, dihydroxyacetone, tumeric oleoresin, cochineal extract, gardenia yellow, gardenia blue, beet powder, grape skin extract, riboflavin, purple sweet potato, red sweet potato, chlorophyll-containing extracts, purple blend (available from Sensient Colors, Inc., No. 53219), carmine high tint, pearlescent pigments, SensiPearl™ Blue, Silver, and Bright Silver (available from Sensient Colors, Inc.), natural colorants, and the like. Other examples of colorants are found in 21 C.F.R. §§ 73 and 74, which are hereby fully incorporated by reference.

In an aspect, the disclosure provides a film coating composition comprising a film forming agent, an opacifying agent, and a complexing agent (e.g., a fatty acid). In embodiments, the disclosed film coating composition can comprise a cellulosic polymer, precipitated calcium carbonate, and oleic acid.

The film coating composition can include at least about 3%, at least about 5%, at least about 10%, at least about 15%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 40%, and at least about 45% film forming agent. The film coating composition can include less than about 60%, less than about 55%, less than about 50%, less than about 45%, less than about 44%, less than about 43%, less than about 42%, less than about 41%, less than about 40%, less than about 39%, less than about 38%, less than about 37%, less than about 36%, less than about 35%, less than about 30%, and less than about 25% film forming agent. This includes, for example, about 3% to about 60%, about 10% to about 50%, and about 20% to about 45% film forming agent. In some embodiments, the film forming agent can comprise a cellulosic polymer. In some embodiments, the cellulosic polymer can comprise a non-ionic cellulosic polymer. In some embodiments, the non-ionic cellulosic polymer can comprise, for example, HPC.

The film coating composition can include at least about 15%, at least about 20%, at least about 25%, at least about 30%, at least about 35%, at least about 40%, at least about 45%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 70%, and at least about 75% opacifying agent. The film coating composition can include less than about 80%, less than about 75%, less than about 70%, less than about 69%, less than about 68%, less than about 67%, less than about 66%, less than about 65%, less than about 64%, less than about 63%, less than about 62%, less than about 61%, less than about 60%, less than about 59%, less than about 58%, less than about 57%, less than about 56%, less than about 55%, less than about 50%, less than about 45%, and less than about 40% opacifying agent. This includes, for example, about 15% to about 80%, about 30% to about 70%, and about 55% to about 65% opacifying agent. In some embodiments, the opacifying agent can comprise, for example, precipitated calcium carbonate.

The film coating composition can include at least about 5%, at least about 6%, at least about 7%, at least about 8%, at least about 9%, at least about 10%, at least about 11%, at least about 12% at least about 13%, at least about 14%, at least about 15%, at least about 16%, at least about 17%, at least about 18%, at least about 19%, at least about 20%, at least about 25%, and at least about 30% fatty acid. The film coating composition can include less than about 40%, less than about 35%, less than about 30%, less than about 25%, less than about 20%, less than about 19%, less than about 18%, less than about 17%, less than about 16%, less than about 15%, less than about 14%, less than about 13%, less than about 12%, less than about 11%, and less than about 10% fatty acid. This includes, for example, about 5% to about 30%, about 7% to about 20%, and about 8% to about 12% fatty acid. In some embodiments, the fatty acid can comprise, for example, oleic acid.

The film coating composition can include a second film forming agent. The film coating composition can include at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, and at least about 20% second film forming agent. The film coating composition can include less than about 25%, less than about 20%, less than about 15%, less than about 14%, less than about 13%, less than about 12%, less than about 11%, less than about 10%, less than about 9%, less than about 8%, less than about 7%, less than about 6%, and less than about 5% second film forming agent. This includes, for example, about 1% to about 20%, about 3% to about 15%, and about 5% to about 9% second film forming agent. In some embodiments, the film coating composition can include the film forming agent and the second film forming agent in a ratio of about 3:1 by weight (first film forming agent:second film forming agent). In some embodiments, the second film forming agent can comprise an ionic cellulosic polymer. In embodiments, the ionic cellulosic polymer can serve to capture dissociation species and/or minimize or prevent dissociation of an opacifying agent. In some embodiments, the ionic cellulosic polymer can comprise, for example, sodium CMC.

The film coating composition can include a lubricant. In some embodiments, the film coating composition can include at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, and at least about 25% lubricant. The film coating composition can include less than about 40%, less than about 35%, less than about 30%, less than about 25%, less than about 24%, less than about 23%, less than about 22%, less than about 21%, less than about 20%, less than about 19%, less than about 18%, less than about 17%, less than about 16%, less than about 15%, and less than about 10% lubricant. This includes, for example, about 5% to about 30%, about 9% to about 24%, and about 15% to about 19% lubricant. In some embodiments, the lubricant can comprise, for example, talc.

The film coating composition can include an antioxidant. In some embodiments, the film coating composition can include at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.2%, at least about 1.5%, at least about 1.6%, at least about 1.7%, at least about 1.8%, at least about 1.9%, at least about 2%, at least about 3%, at least about 4%, and at least about 5% antioxidant. The film coating composition can include less than about 5%, less than about 4%, less than about 3%, less than about 2%, less than about 1%, and less than about 0.1% antioxidant. This includes, for example, about 0.01% to about 5%, about 0.05% to about 1.2%, and about 0.1% to about 1% antioxidant. In some embodiments, the antioxidant can comprise, for example, vitamin E tocopherols, DL-α tocopherol, and/or sodium ascorbate.

In an aspect, the disclosure provides a film coating suspension comprising a film forming agent, an opacifying agent, a fatty acid, and a solvent. In embodiments, the disclosed film coating suspension can comprise a cellulosic polymer, precipitated calcium carbonate, oleic acid, and a solvent. Examples of solvents include, but are not limited to, ethanol, water, and combinations thereof. In some embodiments, the film coating suspension can comprise about 15% to about 22% and about 16% to about 20% solids by weight.

The film coating suspension can include at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, and at least about 15% film forming agent. The film coating suspension can include less than about 20%, less than about 15%, less than about 10%, less than about 9%, less than about 8%, less than about 7%, less than about 6%, less than about 5%, less than about 4%, and less than about 3% film forming agent. This includes, for example, about 1% to about 15%, about 2% to about 10%, and about 3% to about 5% film forming agent. In some embodiments, the film forming agent can comprise a cellulosic polymer. In some embodiments, the cellulosic polymer can comprise a non-ionic cellulosic polymer. In some embodiments, the non-ionic cellulosic polymer can comprise, for example, HPC.

The film coating suspension can include at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20% opacifying agent. The film coating suspension can include less than about 25%, less than about 20%, less than about 15%, less than about 14%, less than about 13%, less than about 12%, less than about 11%, less than about 10%, less than about 9%, less than about 8%, less than about 7%, less than about 6%, and less than about 5% opacifying agent. This includes, for example, about 2% to about 20%, about 4% to about 15%, and about 8% to about 14% opacifying agent. In some embodiments, the opacifying agent can comprise, for example, precipitated calcium carbonate.

The film coating suspension can include at least about 0.5%, at least about 1%, at least about 2%, at least about 3%, at least about 4%, at least about 5%, at least about 6%, and at least about 7% fatty acid. The film coating suspension can include less than about 10%, less than about 9%, less than about 8%, less than about 7%, less than about 6%, less than about 5%, less than about 4%, less than about 3%, less than about 2%, and less than about 1% fatty acid. This includes, for example, about 0.5% to about 7%, about 1% to about 4%, and about 1% to about 3% fatty acid. In some embodiments, the fatty acid can comprise, for example, oleic acid.

The film coating suspension can include a second film forming agent. The film coating suspension can include at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 2%, at least about 3%, at least about 4%, and at least about 5% second film forming agent. The film coating suspension can include less than about 10%, less than about 5%, less than about 4%, less than about 3%, less than about 2%, and less than about 1% second film forming agent. This includes, for example, about 0.1% to about 5%, about 0.5% to about 4%, and about 1% to about 3% second film forming agent. In some embodiments, the film coating suspension can include the film forming agent and the second film forming agent in a ratio of about 3:1 by weight (first film forming agent:second film forming agent). In some embodiments, the second film forming agent can comprise an ionic cellulosic polymer. In embodiments, the ionic cellulosic polymer can serve to capture dissociation species and/or minimize or prevent dissociation of an opacifying agent. In some embodiments, the ionic cellulosic polymer can comprise, for example, sodium CMC.

The film coating suspension can include a lubricant. In some embodiments, the film coating suspension can include at least about 0.5%, at least about 1%, at least about 1.5%, at least about 2%, at least about 2.5%, at least about 3%, at least about 3.5%, and at least about 4% lubricant. The film coating composition can include less than about 10%, less than about 9%, less than about 8%, less than about 7%, less than about 6%, less than about 5%, and less than about 4% lubricant. This includes, for example, about 0.5% to about 8%, about 1% to about 6%, and about 2% to about 5% lubricant. In some embodiments, the lubricant can comprise, for example, talc.

The film coating suspension can include an antioxidant. The film coating suspension can include at least about 0.001%, at least about 0.005%, at least about 0.01%, at least about 0.02%, at least about 0.05%, at least about 0.1%, at least about 0.5%, at least about 1%, at least about 2%, at least about 3%, and at least about 4% antioxidant. The film coating suspension can include less than about 5%, less than about 4%, less than about 3%, less than about 2%, less than about 1%, less than about 0.1%, and less than about 0.01% antioxidant. This includes, for example, about 0.001% to about 4%, about 0.005% to about 3%, and about 0.02% to about 2% antioxidant. In some embodiments, the antioxidant can comprise, for example, vitamin E tocopherols, DL-α tocopherol, and/or sodium ascorbate.

In an aspect, a film coating may be formed on a substrate after application of the disclosed film coating composition or film coating suspension to the substrate, providing a substrate coated with a film coating. The film coating formed on the substrate may contain little or no solvent. In some embodiments, the disclosed film coating can comprise a film forming agent, an opacifying agent, and a fatty acid. In some embodiments, the disclosed film coating can comprise a cellulosic polymer, precipitated calcium carbonate, and oleic acid.

The film coating can include at least about 3%, at least about 5%, at least about 10%, at least about 15%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 40%, and at least about 45% film forming agent. The film coating can include less than about 60%, less than about 55%, less than about 50%, less than about 45%, less than about 44%, less than about 43%, less than about 42%, less than about 41%, less than about 40%, less than about 39%, less than about 38%, less than about 37%, less than about 36%, less than about 35%, less than about 30%, and less than about 25% film forming agent. This includes, for example, about 3% to about 60%, about 10% to about 50%, and about 20% to about 45% film forming agent. In some embodiments, the film forming agent can comprise a cellulosic polymer. In some embodiments, the cellulosic polymer can comprise a non-ionic cellulosic polymer. In some embodiments, the non-ionic cellulosic polymer can comprise, for example, HPC.

The film coating can include at least about 15%, at least about 20%, at least about 25%, at least about 30%, at least about 35%, at least about 40%, at least about 45%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 70%, and at least about 75% opacifying agent. The film coating can include less than about 80%, less than about 75%, less than about 70%, less than about 69%, less than about 68%, less than about 67%, less than about 66%, less than about 65%, less than about 64%, less than about 63%, less than about 62%, less than about 61%, less than about 60%, less than about 59%, less than about 58%, less than about 57%, less than about 56%, less than about 55%, less than about 50%, less than about 45%, and less than about 40% opacifying agent. This includes, for example, about 15% to about 80%, about 30% to about 70%, and about 55% to about 65% opacifying agent. In some embodiments, the opacifying agent can comprise precipitated calcium carbonate.

The film coating can include at least about 5%, at least about 6%, at least about 7%, at least about 8%, at least about 9%, at least about 10%, at least about 11%, at least about 12% at least about 13%, at least about 14%, at least about 15%, at least about 16%, at least about 17%, at least about 18%, at least about 19%, at least about 20%, at least about 25%, and at least about 30% fatty acid. The film coating can include less than about 40%, less than about 35%, less than about 30%, less than about 25%, less than about 20%, less than about 19%, less than about 18%, less than about 17%, less than about 16%, less than about 15%, less than about 14%, less than about 13%, less than about 12%, less than about 11%, and less than about 10% fatty acid. This includes, for example, about 5% to about 30%, about 7% to about 20%, and about 8% to about 12% fatty acid. In some embodiments, the fatty acid can comprise, for example, oleic acid.

The film coating can include a second film forming agent. The film coating can include at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, and at least about 20% second film forming agent. The film coating can include less than about 25%, less than about 20%, less than about 15%, less than about 14%, less than about 13%, less than about 12%, less than about 11%, less than about 10%, less than about 9%, less than about 8%, less than about 7%, less than about 6%, and less than about 5% second film forming agent. This includes, for example, about 1% to about 20%, about 3% to about 15%, and about 5% to about 9% second film forming agent. In some embodiments, the film coating can include the film forming agent and the second film forming agent in a ratio of about 3:1 by weight (first film forming agent:second film forming agent). In some embodiments, the second film forming agent can comprise an ionic cellulosic polymer. In embodiments, the ionic cellulosic polymer can serve to capture dissociation species and/or minimize or prevent dissociation of an opacifying agent. In some embodiments, the ionic cellulosic polymer can comprise, for example, sodium CMC.

The film coating can include a lubricant. In some embodiments, the film coating can include at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, and at least about 25% lubricant. The film coating can include less than about 40%, less than about 35%, less than about 30%, less than about 25%, less than about 24%, less than about 23%, less than about 22%, less than about 21%, less than about 20%, less than about 19%, less than about 18%, less than about 17%, less than about 16%, less than about 15%, and less than about 10% lubricant. This includes, for example, about 5% to about 30%, about 9% to about 24%, and about 15% to about 19% lubricant. In some embodiments, the lubricant can comprise, for example, talc The film coating can include an antioxidant. The film coating can include at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.2%, at least about 1.5%, at least about 1.6%, at least about 1.7%, at least about 1.8%, at least about 1.9%, at least about 2%, at least about 3%, at least about 4%, and at least about 5% antioxidant. The film coating can include less than about 5%, less than about 4%, less than about 3%, less than about 2%, less than about 1%, and less than about 0.1% antioxidant. This includes, for example, about 0.01% to about 15%, about 0.05% to about 12%, and about 0.1% to about 8% antioxidant. In some embodiments, the antioxidant can comprise, for example, vitamin E tocopherols, DL-α tocopherol, and/or sodium ascorbate.

In another aspect, the disclosure provides a film coating composition comprising a film forming agent, an opacifying agent, a plasticizing agent, and a complexing agent (e.g., a polyol). In embodiments, the disclosed film coating compositions can comprise a cellulosic polymer, precipitated calcium carbonate, a plasticizing agent, and xylitol.

The film coating composition can include at least about 3%, at least about 5%, at least about 10%, at least about 15%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 45%, at least about 50%, at least about 55%, at least about 60% film forming agent. The film coating composition can include less than about 60%, less than about 55%, less than about 50%, less than about 45%, less than about 40%, less than about 39%, less than about 38%, less than about 37%, less than about 36%, less than about 35%, less than about 34%, less than about 33%, less than about 32%, less than about 31%, less than about 30%, less than about 29%, less than about 28%, less than about 27%, less than about 26%, less than about 25%, less than about 24%, less than about 23%, less than about 22%, less than about 21%, less than about 20%, less than about 15%, less than about 10%, and less than about 5% film forming agent. This includes, for example, about 3% to about 60%, about 10% to about 50%, and about 20% to about 40% film forming agent. In some embodiments, the film forming agent can comprise a cellulosic polymer. In some embodiments, the cellulosic polymer can include, for example, HPMC.

The film coating composition can include at least about 15%, at least about 20%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 55%, and at least about 60% opacifying agent. The film coating composition can include less than about 70%, less than about 60%, less than about 50%, less than about 45%, less than about 44%, less than about 43%, less than about 42%, less than about 41%, less than about 40%, less than about 39%, less than about 38%, less than about 37%, less than about 36%, less than about 35%, less than about 34%, less than about 33%, less than about 32%, less than about 31%, less than about 30%, less than about 29%, less than about 28%, less than about 27%, less than about 26%, less than about 25%, and less than about 20% opacifying agent. This includes, for example, about 15% to about 80%, about 20% to about 60%, and about 25% to about 45% opacifying agent. In some embodiments, the opacifying agent can include, for example, precipitated calcium carbonate.

The film coating composition can include at least about 1%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, and at least about 30% plasticizing agent. The film coating composition can include less than about 40%, less than about 30%, less than about 25%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, and less than about 5% plasticizing agent. This includes, for example, about 1% to about 30%, about 8% to about 25%, and about 12% to about 18% plasticizing agent. The plasticizing agent can include, for example, medium chain triglycerides, glycerin, and/or stearic acid, and the like.

The film coating composition can include at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, and at least about 25% polyol. The film coating composition can include less than about 30%, less than about 25%, less than about 20%, less than about 15%, less than about 14%, less than about 13%, less than about 12%, less than about 11%, less than about 10%, less than about 9%, less than about 8%, less than about 7%, less than about 6%, and less than about 5% polyol. This includes, for example, about 3% to about 25%, about 5% to about 20%, and about 7% to about 15% polyol. In some embodiments, the polyol can comprise, for example, xylitol.

The film coating composition can include an antioxidant. In some embodiments, the film coating composition can include at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.2%, at least about 1.5%, at least about 1.6%, at least about 1.7%, at least about 1.8%, at least about 1.9%, at least about 2%, at least about 3%, at least about 4%, and at least about 5% antioxidant. The film coating composition can include less than about 5%, less than about 4%, less than about 3%, less than about 2%, less than about 1%, and less than about 0.1% antioxidant. This includes, for example, about 0.01% to about 5%, about 0.05% to about 1.2%, and about 0.1% to about 1% antioxidant. In some embodiments, the antioxidant can comprise, for example, vitamin E tocopherols, DL-α tocopherol, and/or sodium ascorbate.

The film coating composition can include a colorant. The film coating composition can include at least about 0.01%, at least about 0.05%, at least about 0.1%, at least about 0.5%, at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, and at least about 20% colorant. The film coating composition can include less than about 30%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, and less than about 0.1% colorant. This includes, for example, about 0.05% to about 30%, about 0.1% to about 25%, and about 1% to about 20% colorant.

In an aspect, the disclosure provides a film coating suspension comprising a film forming agent, an opacifying agent, a plasticizing agent, a polyol, and a solvent. In embodiments, the disclosed film coating suspension can comprise a cellulosic polymer, precipitated calcium carbonate, a plasticizing agent, xylitol, and a solvent. Examples of solvents include, but are not limited to, ethanol, water, and combinations thereof. In some embodiments, the film coating suspension can comprise about 15% to about 22% and about 16% to about 20% solids by weight.

The film coating suspension can include at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, and at least about 15% film forming agent. The film coating suspension can include less than about 20%, less than about 15%, less than about 12%, less than about 11%, less than about 10%, less than about 9%, less than about 8%, less than about 7%, less than about 6%, and less than about 5% film forming agent. This includes, for example, about 1% to about 15%, about 2% to about 12%, and about 4% to about 8% film forming agent. In some embodiments, the film forming agent can comprise a cellulosic polymer. In some embodiments, the cellulosic polymer can comprise, for example, HPMC.

The film coating suspension can include at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, and at least about 18% opacifying agent. The film coating suspension can include less than about 20%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, and less than about 5% opacifying agent. This includes, for example, about 2% to about 18%, about 3% to about 15%, and about 4% to about 10% opacifying agent. In some embodiments, the opacifying agent can include, for example, precipitated calcium carbonate.

The film coating suspension can include at least about 0.1%, at least about 0.5%, at least about 1%, at least about 2%, at least about 3%, at least about 4%, at least about 5%, at least about 6%, and at least about 7% plasticizing agent. The film coating suspension can include less than about 10%, less than about 9%, less than about 8%, less than about 7%, less than about 6%, less than about 5%, less than about 4%, less than about 3%, less than about 2%, and less than about 1% plasticizing agent. This includes, for example, about 0.1% to about 7%, about 1% to about 6%, and about 1% to about 4% plasticizing agent. The plasticizing agent can include, for example, medium chain triglycerides, glycerin, and/or stearic acid, and the like.

The film coating suspension can include at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 2%, at least about 3%, at least about 4%, at least about 5%, and at least about 6% polyol. The film coating suspension can include less than about 10%, less than about 9%, less than about 8%, less than about 7%, less than about 6%, less than about 5%, less than about 4%, less than about 3%, less than about 2%, and less than about 1% polyol. This includes, for example, about 0.1% to about 6%, about 0.5% to about 5%, and about 1% to about 3% polyol. In some embodiments, the polyol can comprise, for example, xylitol.

The film coating suspension can include an antioxidant. The film coating suspension can include at least about 0.001%, at least about 0.005%, at least about 0.01%, at least about 0.02%, at least about 0.05%, at least about 0.1%, at least about 0.5%, at least about 1%, at least about 2%, at least about 3%, and at least about 4% antioxidant. The film coating suspension can include less than about 5%, less than about 4%, less than about 3%, less than about 2%, less than about 1%, less than about 0.1%, and less than about 0.01% antioxidant. This includes, for example, about 0.001% to about 4%, about 0.005% to about 3%, and about 0.02% to about 2% antioxidant. In some embodiments, the antioxidant can comprise, for example, vitamin E tocopherols, DL-α tocopherol, and/or sodium ascorbate.

The film coating suspension can include a colorant. The film coating suspension can include at least about 0.001%, at least about 0.005%, at least about 0.01%, at least about 0.05%, at least about 0.1%, at least about 0.5%, at least about 1%, at least about 2%, at least about 3%, at least about 4%, and at least about 5% colorant. The film coating suspension can include less than about 5%, less than about 4%, less than about 3%, less than about 2%, less than about 1%, less than about 0.1%, and less than about 0.01% colorant. This includes, for example, about 0.005% to about 7%, about 0.01% to about 5%, and about 0.1% to about 4% colorant.

In an aspect, a film coating may be formed on a substrate after application of the disclosed film coating composition or film coating suspension to the substrate, providing a substrate coated with a film coating. The film coating formed on the substrate may contain little or no solvent. In embodiments, the disclosed film coating can comprise a film forming agent, opacifying agent, a plasticizing agent, and a polyol. In embodiments, the disclosed film coating can comprise a cellulosic polymer, precipitated calcium carbonate, a plasticizing agent, and xylitol.

The film coating can include at least about 3%, at least about 5%, at least about 10%, at least about 15%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 45%, at least about 50%, at least about 55%, at least about 60% film forming agent. The film coating can include less than about 60%, less than about 55%, less than about 50%, less than about 45%, less than about 40%, less than about 39%, less than about 38%, less than about 37%, less than about 36%, less than about 35%, less than about 34%, less than about 33%, less than about 32%, less than about 31%, less than about 30%, less than about 29%, less than about 28%, less than about 27%, less than about 26%, less than about 25%, less than about 24%, less than about 23%, less than about 22%, less than about 21%, less than about 20%, less than about 15%, less than about 10%, and less than about 5% film forming agent. This includes, for example, about 3% to about 60%, about 10% to about 50%, and about 20% to about 40% film forming agent. In some embodiments, the film forming agent can comprise a cellulosic polymer. In some embodiments, the cellulosic polymer can comprise, for example, HPMC.

The film coating can include at least about 15%, at least about 20%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 55%, and at least about 60% opacifying agent. The film coating can include less than about 70%, less than about 60%, less than about 50%, less than about 45%, less than about 44%, less than about 43%, less than about 42%, less than about 41%, less than about 40%, less than about 39%, less than about 38%, less than about 37%, less than about 36%, less than about 35%, less than about 34%, less than about 33%, less than about 32%, less than about 31%, less than about 30%, less than about 29%, less than about 28%, less than about 27%, less than about 26%, less than about 25%, and less than about 20% opacifying agent. This includes, for example, about 15% to about 80%, about 20% to about 60%, and about 25% to about 45% opacifying agent. In some embodiments, the opacifying agent can include, for example, precipitated calcium carbonate.

The film coating can include at least about 1%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, and at least about 30% plasticizing agent. The film coating can include less than about 40%, less than about 30%, less than about 25%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, and less than about 5% plasticizing agent. This includes, for example, about 1% to about 30%, about 8% to about 25%, and about 12% to about 18% plasticizing agent. The plasticizing agent can include, for example, medium chain triglycerides, glycerin, and/or stearic acid, and the like.

The film coating can include at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, and at least about 25% polyol. The film coating can include less than about 30%, less than about 25%, less than about 20%, less than about 15%, less than about 14%, less than about 13%, less than about 12%, less than about 11%, less than about 10%, less than about 9%, less than about 8%, less than about 7%, less than about 6%, and less than about 5% polyol. This includes, for example, about 3% to about 25%, about 5% to about 20%, and about 7% to about 15% polyol. In some embodiments, the polyol can comprise, for example, xylitol.

The film coating can include an antioxidant. The film coating can include at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.2%, at least about 1.5%, at least about 1.6%, at least about 1.7%, at least about 1.8%, at least about 1.9%, at least about 2%, at least about 3%, at least about 4%, and at least about 5% antioxidant. The film coating can include less than about 5%, less than about 4%, less than about 3%, less than about 2%, less than about 1%, and less than about 0.1% antioxidant. This includes, for example, about 0.01% to about 15%, about 0.05% to about 12%, and about 0.1% to about 8% antioxidant. In some embodiments, the antioxidant can comprise, for example, vitamin E tocopherols, DL-α tocopherol, and/or sodium ascorbate.

The film coating can include a colorant. The film coating can include at least about 0.01%, at least about 0.05%, at least about 0.1%, at least about 0.5%, at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, and at least about 20% colorant. The film coating can include less than about 30%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, and less than about 0.1% colorant. This includes, for example, about 0.05% to about 30%, about 0.1% to about 25%, and about 1% to about 20% colorant.

In an aspect, a top coat can be applied to the disclosed film coatings. The top coat may include medium chain triglycerides, HPMC, and inulin (for example, Spectrablend™ II Clear, available from Sensient Technologies, Inc.). The top coat may further comprise a colorant. The top may comprise at least about 0.1%, at least about 0.5%, at least about 0.75%, at least about 1%, and at least about 2% colorant. The top coat may comprise less than about 5%, less than about 2%, less than about 1%, and less than about 0.5% colorant. This includes, for example, about 0.1% to about 5%, about 0.5% to about 3%, and about 0.75% to about 2% colorant. The top coat may enhance gloss, slip, and/or gleam of a coated substrate, and the top coat may also stabilize colorants. In some embodiments, the top coat can be prepared at about 6% to about 15% solution solids and about 8% to about 10% solution solids.

The disclosed film coating suspension may suitably exhibit low viscosity and/or high solution solids content. Thus, embodiments provide a coating suspension that exhibits a low viscosity relative to the amount of solids content. In some embodiments, the disclosed film coating suspensions may include high solution solids content. Suitably, a film coating suspension having high solution solids content may include, for example, at least about 5% solids, at least about 15%, and at least about 20% solution solids. In some embodiments, the disclosed film coating suspensions may have low viscosity. Suitably, film coating suspension having low viscosity may have viscosity of less than about 400 centipoise (cps), less than about 300 cps, less than about 250 cps, less than about 200 cps, less than about 150 cps, and less than about 100 cps. In some embodiments, the disclosed film coating suspensions may have high solution solids content and low viscosity. Suitably, the film coating suspensions may have at least about 5% solids, at least about 15%, and at least about 20% solution solids and viscosity of less than about 400 cps, less than about 300 cps, less than about 250 cps, less than about 200 cps, less than about 150 cps, and less than about 100 cps. For example, in some embodiments, the disclosed film coating suspensions can exhibit viscosity of less than about 300 cps at 20% solids. The disclosed film coating suspensions may have lower viscosity than a traditional film coating with the same solution solids percentage. In some embodiments, the disclosed film coating suspensions comprise a film forming agent, an opacifying agent, and a complexing agent in amounts sufficient to confer a film coating suspension with lower viscosity than a traditional film coating with the same solution solids percentage.

Viscosity may be assessed by any suitable method such as, for example, using a Brookfield viscometer equipped with a UL Adapter Assembly and UL Spindle (available from Brookfield Engineering Labs., Inc.). The film coating suspension or other test sample is poured into a clean graduated cylinder or other sample container, and the spindle is immersed in the sample. After starting the viscometer motor, the speed is adjusted to achieve a percent torque between 50-70%, and the viscosity (cps) of the sample is recorded.

The disclosed film coatings may exhibit high whiteness and/or high opacity. Whiteness can be assessed by any suitable method, such as, for example, measuring the Whiteness Index according to ASTM Method E313 with a D65/10° illumination source (referred to as "WI E313 [D65/10]") using a LabScan™ XE spectrophotometer (available from HunterLab, Inc.). A sample substrate coated with a film coating is loaded into the instrument's sample port and scanned, and the Whiteness Index (WI E313 [D65/10]) value is calculated using measurements taken on the CIE L*a*b* color scale. The resulting Whiteness Index value is used to assess whiteness of the sample. Suitably, the disclosed film coatings can yield high WI E313 [D65/10] values of at least about 50, at least about 55, at least about 60, at least about 65, at least about 70, at least about 75, at least about 80, at least about 85, and at least about 90. Opacity can also be assessed by evaluating the Whiteness Index achieved upon coating one or more colored substrate cores with film coatings as described herein. For example, when coating a colored substrate, the Whiteness Index will increase with additional weight gain until high and/or full opacity is reached. Upon reaching high and/or full opacity, the Whiteness Index may level off relative to further increases in weight gain. Suitably, the disclosed film coatings can suitably provide high and/or full opacity at a weight gain of less than about 10%, less than about 9%, less than about 8%, less than about 7%, less than about 6%, less than about 5%, and less than about 4% weight gain, for example, about 3% to about 10% weight gain. In some embodiments, the disclosed film coating compositions, film coating suspensions, and/or film coatings comprise an opacifying agent and a complexing agent in amounts sufficient to provide a film coating with high whiteness and/or full/high opacity at low weight gain.

The disclosed film coatings may exhibit high brightness. Brightness can assessed by any suitable method, such as, for example, using a LabScan™ XE spectrophotometer to measure the amount of light reflected at 457 nm. A sample substrate coated with a film coating is loaded into the instrument's sample port and scanned, and the resulting reflectance at 457 nm is used to assess brightness of the sample. Suitably, the disclosed film coatings can yield a high brightness value of at least about 80, at least about 81, at least about 82, at least about 83, at least about 84, at least about 85, at least about 86, at least about 87, at least about 88, at least about 89, and at least about 90. In some embodiments, the disclosed film coating compositions, film coating suspensions, and/or film coatings comprise an opacifying agent and a complexing agent in amounts sufficient to provide a film coating with high brightness.

The disclosed film coatings may exhibit low yellowness. Yellowness can be assessed by any suitable method, such as, for example, measuring the Yellowness Index according to ASTM Method E313 with a D65/10° illumination source (referred to as "YI E313 [D65/10]") using a LabScan™ XE spectrophotometer. A sample substrate coated with a film coating is loaded into the instrument's sample port and scanned, and the resulting YI E313 [D65/10] value is used to assess yellowness of the sample. Suitably, the disclosed film coatings can yield low YI E313 [D65/10] values of less than about 20, less than about 19, less than about 18, less than about 17, less than about 16, less than about 15, less than about 14, less than about 13, less than about 12, less than about 11, less than about 10, less than about 9, less than about 8, less than about 7, less than about 6, and less than about 5. In some embodiments, the disclosed film coating compositions, film coating suspensions, and/or film coatings comprise an opacifying agent and a complexing agent in amounts sufficient to provide a film coating with low yellowness.

The disclosed film coatings may exhibit high stability. Stability can be assessed via any suitable method, such as, for example, measuring discoloration of a substrate coated with a film coating over time under various storage conditions. For example, a substrate coated with a film coating can be stored at 25° C. under 60% relative humidity ("storage condition H2") or at 40° C. under 75% relative humidity ("storage condition H4"), and the WI E313 [D65/10] value and/or the $\Delta E^*$ value can be measured at various intervals, such as, for example, 7 days, 10 days, 14 days, 17 days, 25 days, 1 month, 2 months, 3 months, etc., using a LabScan™ XE spectrophotometer. Stable Whiteness Index values measured over time can indicate stability of a film coating under a given storage condition, and changes in the WI E313 [D65/10] can indicate discoloration and instability. For example, changes in Whiteness Index during storage of less than about 10%, less than about 9%, less than about 8%, less than about 7%, less than about 6%, less than about 5%, less than about 4%, less than about 3%, less than about 2%, and less than about 1% can indicate high stability. In addition, a $\Delta E^*$ value can be used to assess stability of a film coating. Large $\Delta E^*$ values and/or $\Delta E^*$ values increasing over time can indicate discoloration or instability of a film coating under a given storage condition. Conversely, a low $\Delta E^*$ value can indicated high stability. For example, a $\Delta E^*$ value of less than about 5, less than about 4, less than about 3, less than about 2, less than about 1, and less than about 0.5 can indicate high stability. In some embodiments, the disclosed film coating compositions, film coating suspensions, and/or film coatings comprise a film forming agent, an opacifying agent, a complexing agent, and/or a plasticizing agent in amounts sufficient to provide a film coating with high stability.

The disclosed film coatings may exhibit strong adhesion to a substrate. Adhesion of the dry film coatings may be measured using a TA.XT Plus Texture Analyzer (available from Texture Technologies Corp.) equipped with a 25 mm stainless steel cylindrical probe. A round placebo tablet coated with a coating is scored around its hemisphere with a sharp blade and then attached to the top of the flat platform of the texture analyzer using heavy-duty double-sided tape (available from 3M). Another piece of heavy-duty double-sided tape is pressed to the bottom of the cylindrical probe, and the probe is then compressed to 800 g force onto the softgel for 10 seconds. The probe is then pulled away from the softgel at a rate of 1 mm/second, measuring the tension force until either (1) the coating separates from the softgel, or (2) the tape separates from the coating. Where the coating remains on the substrate, the measured force equals the force required to pull the double-sided tape away from the coating, and the adhesion force of the coating to the softgel is thus greater than the measured adhesion force between the tape and the coating. Suitably, a dry film coating having strong adhesion may exhibit an adhesion force between the coating and the placebo tablet of at least about 0.5, at least about 0.6, at least about 0.7, at least about 0.8, at least about 0.9, at least about 1, at least about 1.1, at least about 1.2, at least about 1.3, at least about 1.4, at least about 1.5, at least about 1.6, at least about 1.7, at least about 1.8, at least about 1.9, or at least about 2 g force. This includes, for example, about 0.8 g force to about 1.5 g force and about 1.1 g force to about 1.3 g force.

The compositions and suspensions described herein can be manufactured using techniques and equipment that are known and commonly used in the art. Equipment known in the industry for standard tablet coating are Thomas Engineering, Inc., and Vector Corporation HiCoater® tablet coating systems. Manufacturing steps such as order of component addition, mixing temperatures (heating and/or cooling), mixing time, mixing speed, etc. can be driven by either by formulation or equipment requirements, or both. A number of parameters can be modified during the manufacturing process without substantial effect on the efficacy of the resulting product. The manufacturing methods and processes can further include separate steps for validating the resulting composition (e.g., the total amounts, ratios, and even distribution of components in the composition, etc.).

In an aspect, the film coating suspension may be formed as follows. Components of a film coating composition comprising at least one of a film forming agent, an opacifying agent, a complexing agent, a plasticizing agent, a lubricant, an antioxidant, a colorant, and combinations thereof may be mixed with, for example, a plow mixer (available from Littleford Day Inc.; Florence Ky.). If included, one or more plasticizing agents may be added last to the film coating composition. Solvent (e.g., water) may be added to a mixing tank equipped with a low-shear overhead mixer (available from Littleford Day, Inc.; Florence Ky.) and brought to a medium vortex. In some embodiments, the mixing blade can span at least about ⅓ the diameter of the mixing tank. The film coating composition may be added into the medium vortex, and mixing may continue for at least about 30 minutes and/or until the suspension achieves a smooth consistency with no visible lumps.

Methods, processes, and techniques for coating a substrate including applying a film coating suspension to a substrate to form a film coating thereon are provided. In some embodiments, a coating pan may be charged with a substrate such as, for example, capsules, tablets, and/or softgels. In some embodiments, the bed may be warmed to about 33° C. to about 40° C. The processing parameters may be as set forth below.

The disclosed film coating suspensions may, at a suitable concentration which is system dependent, be applied (e.g., sprayed) using commercially available equipment to form a film coating on a substrate. In some embodiments, the coating methods can include applying a film coating suspension to a substrate to a weight gain of less than about 10%, less than about 9%, less than about 8%, less than about 7%, less than about 6%, less than about 5%, and less than about 4% weight gain, for example, about 3% to about 10% weight gain. In some embodiments, the film coating suspension may be applied to a substrate by loading substrate into a vented coating pan, such as, for example, a 15-inch, 24-inch, 48-inch, or 60-inch side-vented coating pan. The inlet temperature may be at least about 45° C., at least about 50° C., at least about 55° C., at least about 58° C., at least about 60° C., at least about 65° C., and at least about 70° C. The inlet temperature may be less than about 75° C., less than about 70° C., less than about 65° C., and less than about 60. This includes, for example, about 50° C. to about 75° C., about 50 to about 65° C., and about 55° C. to about 75° C. The outlet temperature may be at least about 32° C., at least about 35° C., at least about 40° C., and at least about 45° C. The outlet temperature may be less than about 55° C., less than about 50° C., less than about 50° C., and less than about 45° C. This includes, for example, about 32° C. to about 55° C., about 35° C. to about 45° C., and about 40° C. to about 50° C. The atomizing air pressure may be at least about 20 psi, at least about 21 psi, at least about 25 psi, at least about 30 psi, at least about 35 psi, at least about 40 psi, at least about 45 psi, at least about 50 psi, and at least about 55 psi. The atomizing air pressure may be less than about 75 psi, less than about 70 psi, less than about 65 psi, less than about 60 psi, less than about 55 psi, less than about 50 psi, less than about 40 psi, and less than about 30 psi. This includes, for example, about 20 to about 75 psi, about 21 to about 23 psi, about 25 to about 30 psi, about 50 to about 55 psi, and about 50 to about 70 psi. The coating time may be from about 5 minutes to about 3 hours. The film coating suspension can be allowed to dry, forming a film coating on the substrate. Exemplary coating parameters are provided in Table 1.

TABLE 1

Exemplary coating parameters.

| Pan Size | 15 inch | 24 inch | 48 inch | 60 inch |
| --- | --- | --- | --- | --- |
| Air volume (cfm) | 280-320 | 440-520 | 2200-2400 | 3800-4800 |
| Inlet temp. (° C.) | 50-65 | 50-65 | 55-75 | 55-75 |
| Outlet temp. (° C.) | 35-45 | 35-45 | 40-50 | 40-50 |
| Bed temp. (° C.) | 33-44 | 33-44 | 35-47 | 35-47 |
| Pre-warm temp. (° C.) | 30-40 | 30-40 | 30-40 | 30-45 |
| Spray rate (g/min) | 15-20 | 20-60 | 450-650 | 600-1000 |
| Atomizing air pressure (psi) | 21-23 | 25-30 | 50-55 | 50-70 |
| Pattern air pressure (psi) | 25 | 35 | 50-60 | 50-75 |
| No. of guns | 1 | 2 | 3-4 | 4-6 |
| Pan speed (rpm) | 15-20 | 12-15 | 5-10 | 4-6 |
| Pan charge weight (kg) | 1-3 | 15-20 | 120-200 | 250-350 |

The disclosed film coatings may be flexible with tensile strength. The film coatings may be consistent batch-to-batch, may meet current FDA regulations for dietary supplements, may be robust (easy to use and prepare), and may coat various surfaces (softgels, capsules, tablets, gelatin, vegetable, etc). The film coating may be cost effective and economical. Substrates coated with the disclosed film coatings may pass an immediate release disintegration test, such as, for example, USP32/NF27 S2, Chapter 2040 (Disintegration and Dissolution of Dietary Supplements), Chapter 701 (Disintegration) testing criteria. In some embodiments, the film coatings can be GRAS (Generally Recognized as Safe) and may be vegetarian. The film coatings may be able to be applied at a fast rate and broad temperature while providing good film adhesion and flexibility.

The film coating compositions may be used in food, pharmaceutical or nutraceutical applications intended for use in mammals, including, without limitation, rodents, canines, felines, non-human primates, ungulates, and humans. They can be used to coat pharmaceutical or non-pharmaceutical dosage units.

EXAMPLES

Materials. Inulin preparations including Orafti® P95 and Orafti® HSI (available from BENEO, Inc.). Neobee® M-5 medium chain triglycerides from fractionated coconut oil (available from Stepan Co.). HPMC preparations including HPMC 3, HPMC 5, HPMC 6, and HPMC 15, wherein the numbers 3, 5, 6, and 15 indicate the HPMC preparation's viscosity in 1% aqueous solution (i.e., "HPMC 3" indicates an HPMC preparation that exhibits a viscosity of 3 cps when mixed with water to make a 1% (w/w) HPMC solution). Commercially available examples include Spectracel™ 3, 5, 6, and 15 (available from Sensient Technologies). HPC (available from Ashland Aqualon, Inc.). Sodium CMC (available from Ashland Aqualon, Inc.). Precipitated calcium carbonate preparations including ViCALity™ (available from Specialty Minerals, Inc.). Oleic acid preparations (available from Acme-Hardesty Oleochemicals). Xylitol preparations (available from Roquette).

Exemplary embodiments of the disclosure are provided in the following examples. These embodiments of the disclosure were produced and evaluated as indicated, using materials, compositions, suspensions, coatings, and methods as described herein. The following examples are provided merely to illustrate certain embodiments of the disclosure and to assist one of ordinary skill in making and using the same, are not to be interpreted to limit the scope of the disclosure or the appended claims.

Example 1

| Material | % Film Coating Composition |
| --- | --- |
| HPC | 21.6 |
| Sodium CMC | 7.2 |
| Precipitated Calcium Carbonate | 60.39 |
| Vitamin E Tocopherols | 0.11 |
| Oleic Acid | 10.7 |
| Total | 100% |

Example 2

| Material | % Film Coating Composition |
| --- | --- |
| HPC | 21.6 |
| Sodium CMC | 7.2 |
| Precipitated Calcium Carbonate | 60.4 |
| Oleic Acid | 10.8 |
| Total | 100% |

Example 3

| Material | % Film Coating Composition |
| --- | --- |
| HPC | 21.6 |
| Sodium CMC | 7.2 |
| Precipitated Calcium Carbonate | 60.3 |
| DL-α-Tocopherol | 0.1 |
| Oleic Acid | 10.7 |
| Total | 100% |

Example 4

| Material | % Film Coating Composition |
| --- | --- |
| HPMC 6 | 40 |
| Xylitol | 15 |
| Precipitated Calcium Carbonate | 26 |
| Medium Chain Triglycerides | 18 |
| Blue No. 2 | 1 |
| Total | 100% |

Example 5

| Material | % Film Coating Composition |
| --- | --- |
| HPC | 40 |
| Xylitol | 15 |
| Precipitated Calcium Carbonate | 26 |
| Medium Chain Triglycerides | 18 |
| Purple Sweet Potato | 1 |
| Total | 100% |

Example 6

| Material | % Film Coating Composition |
| --- | --- |
| HPMC 6 | 40 |
| Xylitol | 15 |
| Precipitated Calcium Carbonate | 26 |
| Medium Chain Triglycerides | 8 |
| Glycerin | 10 |
| Purple Sweet Potato | 1 |
| Total | 100% |

Example 7 (Green)

| Material | % Film Coating Composition |
|---|---|
| HPMC 6 | 39.3 |
| Xylitol | 14.4 |
| Precipitated Calcium Carbonate | 25.1 |
| Medium Chain Triglycerides | 16.9 |
| Purple Sweet Potato | 4.2 |
| Beta Carotene | 0.1 |
| Total | 100% |

Example 8 (Green)

| Material | % Film Coating Composition |
|---|---|
| HPMC 6 | 38.5 |
| Xylitol | 14.4 |
| Precipitated Calcium Carbonate | 25.1 |
| Glycerin | 16.9 |
| Purple Sweet Potato | 4.2 |
| Beta Carotene | 0.9 |
| Total | 100% |

Example 9 (Green)

| Material | % Film Coating Composition |
|---|---|
| HPMC 6 | 38.5 |
| Xylitol | 14.4 |
| Precipitated Calcium Carbonate | 25.1 |
| Glycerin | 16.9 |
| Purple Sweet Potato | 0.9 |
| Beta Carotene | 4.2 |
| Total | 100% |

Example 10 (Natural Green)

| Material | % Film Coating Composition |
|---|---|
| HPMC 6 | 21.6 |
| Xylitol | 14.4 |
| Precipitated Calcium Carbonate | 25.1 |
| Medium Chain Triglycerides | 16.9 |
| Purple Sweet Potato | 0.5 |
| Beta Carotene | 4.6 |
| Total | 100% |

Example 11 (Natural Green)

| Material | % Film Coating Composition |
|---|---|
| HPMC 6 | 38.5 |
| Xylitol | 14.4 |
| Precipitated Calcium Carbonate | 25.1 |
| Medium Chain Triglycerides | 16.9 |
| Purple Sweet Potato | 0.72 |
| Beta Carotene | 4.35 |
| Total | 100% |

Example 12 (Natural Green)

| Material | % Film Coating Composition |
|---|---|
| HPMC 6 | 36.87 |
| Xylitol | 13.58 |
| Precipitated Calcium Carbonate | 24.26 |
| Medium Chain Triglycerides | 16.5 |
| Beta Carotene | 5.86 |
| Purple Blend | 2.93 |
| Total | 100% |

Example 13 (Natural Blue)

| Material | % Film Coating Composition |
|---|---|
| HPMC 6 | 46.14 |
| Xylitol | 7.22 |
| Precipitated Calcium Carbonate | 31.82 |
| Medium Chain Triglycerides | 10.77 |
| Purple Blend | 4.06 |
| Total | 100% |

Example 14 (Pink)

| Material | % Film Coating Composition |
|---|---|
| HPMC 6 | 35 |
| Xylitol | 8.08 |
| Precipitated Calcium Carbonate | 41 |
| Medium Chain Triglycerides | 15.8 |
| Carmine high tint 50% | 0.12 |
| Total | 100% |

Example 15 (White)

| Material | % Film Coating Composition |
|---|---|
| HPMC 6 | 35 |
| Xylitol | 8.2 |
| Precipitated Calcium Carbonate | 41 |
| Medium Chain Triglycerides | 15.8 |
| Total | 100% |

Example 16

| Material | % Film Coating Composition |
|---|---|
| HPMC 6 | 43 |
| Xylitol | 10 |
| Precipitated Calcium Carbonate | 35 |
| Medium Chain Triglycerides | 12 |
| Total | 100% |

Example 17

| Material | % Film Coating Composition |
|---|---|
| HPMC 6 | 48.1 |
| Xylitol | 7.51 |
| Precipitated Calcium Carbonate | 33.17 |
| Medium Chain Triglycerides | 11.22 |
| Total | 100% |

Example 18

| Material | % Film Coating Composition |
|---|---|
| HPMC 6 | 30 |
| Xylitol | 15 |
| Precipitated Calcium Carbonate | 15 |
| Medium Chain Triglycerides | 12 |
| Talc | 24 |
| Water | 4 |
| Total | 100% |

Example 19

| Material | % Film Coating Composition |
|---|---|
| HPMC 6 | 30 |
| Xylitol | 15 |
| Precipitated Calcium Carbonate | 30 |
| Medium Chain Triglycerides | 12 |
| Talc | 9 |
| Water | 4 |
| Total | 100% |

Example 20

| Material | % Film Coating Composition |
|---|---|
| HPMC 6 | 30 |
| Xylitol | 15 |
| Precipitated Calcium Carbonate | 38 |
| Medium Chain Triglycerides | 12 |
| Stearic Acid | 1 |
| Water | 4 |
| Total | 100% |

Example 21

| Material | % Film Coating Composition |
|---|---|
| HPMC 6 | 30 |
| Xylitol | 15 |
| Precipitated Calcium Carbonate | 20 |
| Medium Chain Triglycerides | 12 |
| Talc | 19 |
| Water | 4 |
| Total | 100% |

Example 22

| Material | % Film Coating Composition |
|---|---|
| HPMC 6 | 40 |
| Xylitol | 15 |
| Precipitated Calcium Carbonate | 26 |
| Medium Chain Triglycerides | 19 |
| Total | 100% |

Example 23

| Material | % Film Coating Composition |
|---|---|
| HPMC 6 | 40 |
| Inulin | 8 |
| Precipitated Calcium Carbonate | 33 |
| Medium Chain Triglycerides | 19 |
| Total | 100% |

Example 24

| Material | % Film Coating Composition |
|---|---|
| HPMC 6 | 40 |
| Maltitol | 15 |
| Precipitated Calcium Carbonate | 26 |
| Medium Chain Triglycerides | 19 |
| Total | 100% |

Example 25—Coating Whiteness and Opacity

White placebo tablet cores were coated to 6%, 8.6%, and 13% weight gain using a film coating composition according to Example 15 suspended and applied according to spray coating methods described herein. The Whiteness Index (WI E313 [D65/10]) of the coated tablets were measured using a HunterLab LabScan™ XE as described.

TABLE 2

| Sample | L* | a* | b* | ΔE* | WI E313 [D65/10] |
|---|---|---|---|---|---|
| uncoated placebo | 97.47 | −0.46 | 2.87 | | 80.84 |
| coated; 6% weight gain | 92.88 | −0.2 | 0.45 | 5.19 | 80.6 |
| coated; 8.6% weight gain | 96.98 | −0.1 | 3.78 | 1.09 | 75.55 |
| coated, 13% weight gain | 97.3 | −0.17 | 3.24 | 0.5 | 78.77 |

Brown tablet cores were coated to 6%, 8.6%, 10.6%, and 13% weight gain using a film coating composition according to Example 15 suspended and applied according to spray coating methods described herein. The Whiteness Index (WI E313 [D65/10]) of the coated tablets were measured using a HunterLab LabScan™ XE as described. The Whiteness Index was observed to level off with a weight gain of at least about 8.6%, indicating high/full opacity was reached by 8.6% weight gain.

TABLE 3

| Sample | L* | a* | b* | ΔE* | WI E313 [D65/10] |
|---|---|---|---|---|---|
| coated; 6% weight gain | 89.86 | 0.45 | 1.91 | | 66.96 |
| coated; 8.6% weight gain | 92.26 | 0.01 | 1.22 | 2.53 | 75.63 |
| coated; 10.6% weight gain | 92.59 | 0.02 | 1.55 | 2.78 | 74.83 |
| coated, 13% weight gain | 93.12 | −0.17 | 1.52 | 3.33 | 76.23 |

Example 26—Coating Stability

Whiteness Index and Tint Index were used to assess stability of a film coating. Tablet core substrates were coated using a film coating composition according to Example 22 suspended and applied according to spray coating methods described herein. The resulting coated substrates were subjected to storage conditions H2 (25° C. and 60% humidity) or H4 (40° C. and 75% humidity) and measured for discoloration using a HunterLab LabScan™ XE on days 1, 7, 10, 14, and 17. Whiteness Index (WI E313 [D65/10]), Tint Index (Tint E313 [D65/10]), and ΔE* were measured and used as indicators of stability as a function of time and storage condition. Additional sample substrates coated using the film coating composition of Example 22 plus a top coat were also tested in parallel.

TABLE 4

| Coating | L* | a* | b* | ΔE* | Tint E313 [D65/10] | WI E313 [D65/10] | Condition | Day |
|---|---|---|---|---|---|---|---|---|
| Example 22 | 92.05 | −0.05 | 4.51 | n/a | −1.66 | 59.8 | n/a | 0 |
| Example 22 | 91.5 | 0.03 | 5.1 | 0.81 | −2.02 | 55.71 | H2 | 7 |
| Example 22 | 91.14 | 0.06 | 5.55 | 1.39 | −2.26 | 52.71 | H2 | 10 |
| Example 22 | 91.64 | 0.01 | 5.66 | 1.22 | −2.2 | 53.43 | H2 | 14 |
| Example 22 | 91.07 | 0.04 | 5.73 | 1.57 | −2.3 | 51.69 | H2 | 17 |
| Example 22 | 91.45 | 0.33 | 6.65 | 2.26 | −3.16 | 48.33 | H4 | 7 |
| Example 22 | 90.57 | 0.3 | 6.38 | 2.41 | −3.03 | 47.42 | H4 | 10 |
| Example 22 | 91.76 | −0.12 | 7.06 | 2.57 | −2.52 | 47.15 | H4 | 14 |
| Example 22 | 90.16 | −0.18 | 7.63 | 3.65 | −2.67 | 40.45 | H4 | 17 |
| Example 22 + Top Coat | 90.5 | 0.53 | 4.77 | n/a | −2.8 | 54.87 | n/a | 0 |
| Example 22 + Top Coat | 91.38 | 0.69 | 5.66 | 1.26 | −3.4 | 52.83 | H2 | 7 |
| Example 22 + Top Coat | 87.7 | 0.66 | 5.83 | 3 | −3.54 | 43.2 | H2 | 10 |
| Example 22 + Top Coat | 92.24 | 0.62 | 5.65 | 1.94 | −3.25 | 55 | H2 | 14 |
| Example 22 + Top Coat | 90.2 | 0.63 | 6.13 | 1.4 | −3.52 | 47.71 | H2 | 17 |
| Example 22 + Top Coat | 90.25 | 0.41 | 6.08 | 1.34 | −3.11 | 48.05 | H4 | 7 |
| Example 22 + Top Coat | 91.45 | 0.16 | 7.16 | 2.59 | −3.06 | 45.91 | H4 | 10 |

TABLE 4-continued

| Coating | L* | a* | b* | ΔE* | Tint E313 [D65/10] | WI E313 [D65/10] | Condition | Day |
|---|---|---|---|---|---|---|---|---|
| Example 22 + Top Coat | 92.51 | 0.06 | 8.12 | 3.93 | −3.22 | 44.14 | H4 | 14 |
| Example 22 + Top Coat | 91.55 | 0.13 | 9.41 | 4.77 | −3.87 | 35.64 | H4 | 17 |

No significant changes in ΔE* were detected under either storage condition, and no significant changes in WI E313 [D65/10] were detected under condition H2.

What is claimed is:

1. A substrate coated with a film coating, the film coating comprising a film coating composition comprising:
   a) about 3% to about 60% by weight hydroxypropyl methyl cellulose (HPMC);
   b) about 3% to about 25% by weight of polyol;
   c) a plasticizing agent comprising medium chain triglycerides; and
   d) about 15% to about 60% by weight of an opacifying agent;
   wherein the film coating is present in an amount of about 3% to about 10% of the weight of the substrate, and provides a Whiteness Index E313 [D65/10] value of at least 50.

2. The substrate of claim 1, wherein the polyol is selected from the group consisting of xylitol, maltitol, sorbitol, mannitol, erythritol, lactitol, and combinations thereof.

3. The substrate of claim 1, wherein the polyol comprises xylitol.

4. The substrate of claim 1, wherein the polyol is present in the composition in an amount from about 5% to about 20% of the composition by weight.

5. The substrate of claim 1, wherein the plasticizing agent further comprises glycerin, propylene glycol dicaprylate/dicaprate, polyethylene glycol, stearic acid, triethylcitrate, or a combination thereof.

6. The substrate of claim 1, wherein the plasticizing agent is present in the composition in an amount from about 1% to about 30% of the composition by weight.

7. The substrate of claim 1, wherein the opacifying agent comprises precipitated calcium carbonate.

8. The substrate of claim 1, wherein the film coating composition further comprises a fatty acid.

9. The substrate of claim 8, wherein the fatty acid comprises oleic acid.

10. The substrate of claim 1, wherein the film coating composition further comprises a film forming agent.

11. The substrate of claim 10, wherein the film forming agent comprises an ionic cellulosic polymer.

12. The substrate of claim 11, wherein the ionic cellulosic polymer comprises sodium carboxymethylcellulose.

13. The substrate of claim 10, wherein the hydroxypropyl methyl cellulose and the film forming agent are present in a ratio of about 3:1 by weight.

14. The substrate coated with a film coating of claim 1, wherein the substrate comprises a nutritional supplement, a pharmaceutical, a tablet, a capsule, a softgel, a granule, a particle, a food confectionary form, or a seed.

* * * * *